United States Patent [19]

Grayson et al.

[11] 4,093,420
[45] June 6, 1978

[54] MINERAL PROSPECTING BY ORGANIC DIAGENESIS

[75] Inventors: John F. Grayson, Tulsa, Okla.; Peter K. H. Groth, Denver, Colo.

[73] Assignee: Standard Oil Company (Indiana), Chicago, Ill.

[21] Appl. No.: 692,825

[22] Filed: Jun. 4, 1976

[51] Int. Cl.² ............................................. G01N 33/24
[52] U.S. Cl. ............................................... 23/230 EP
[58] Field of Search ................................... 23/230 EP

[56] References Cited

PUBLICATIONS

C. C. M. Gutjahr, Carbonization Measurements of Pollen-Grains and Spores and Their Application, Doctorate Thesis, U. of Leiden, Jun. 1966.
Grayson, J. F., Relationship of Palynomorph Translucency to Carbon and Hydrocarbons in Clastic Sediments, Centre National de la Recherche Scientifique at Paris 15-17, Sep. 1973.

*Primary Examiner*—Robert M. Reese
*Attorney, Agent, or Firm*—Robert B. Stevenson; Arthur McIlroy

[57] ABSTRACT

This is a method of prospecting for accumulations of hydrocarbons or other minerals. At least two (and preferably more) samples of subsurface rock units are taken at different vertical depths in a plurality of locations. Each such sample is processed to recover organic material present in the rocks. From this organic residue, a number of specimens of the same palynomorph taxon are selected, and a characteristic of light absorbed or transmitted by the specific organic particles is determined. The difference in the values obtained in the same location for two sets of palynomorphs at different vertical distances (preferably same well) is called the translucency differential. This differential or the gradient (differential divided by the corresponding vertical distance between sampling points) is then plotted on a map at the location of the various points of sample collection, and a contour map or cross section is drawn. We have found that this contouring tends to produce anomalies comparable to those obtained in seismic prospecting or in magnetic or gravimetric prospecting in that they tend to form "ovals" above the location of a more deep-seated mineral deposit. Accordingly, one employs the anomalies found from the contouring of the data to aid in the location of hydrocarbons or other mineral deposits.

6 Claims, 4 Drawing Figures

MINERAL PROSPECTING BY ORGANIC DIAGENESIS

BACKGROUND OF THE INVENTION

1. Field of the Invention

C.C.M. Gutjahr, in his paper "Carbonization Measurements of Pollen-Grains and Spores and Their Application", Doctorate Thesis at the University of Leiden, June, 1966, studied the degree of carbonization of pollen grains and spores in geologic specimens, pointing out that this could be employed to determine organic diagenesis in areas or intervals devoid of coal. The degree of carbonization of palynomorphs is indeed an index of the level of organic metamorphism to which also other organic matter in the sediment has been subjected, including the precursors of petroleum. Among the factors causing carbonization which have been reported are temperature, time pressure and radioactivity, and of these, particular importance is on the time-temperature relationship of the specimens being investigated. Gutjahr estimated the degree of diagenesis in coals using the measurement of absorption of light by the palynomorph exine. Of course, since percentage of absorption is simply the converse of percentage translucency, either measurement could be employed in carbonization studies. Gutjahr also pointed out the desirability of using standard chemical preparation techinques to prepare the specimens for study and cautioned palynologists of the importance of selecting a type for study that will give low-absorption values when slightly carbonized.

While the date in Gutjahr's thesis was limited to the correlation between the carbonization of pollen grains and spores and the diagenesis found in the metamorphism of coals, he speculated that other correlations with sediment properties might be obtained, such as the use of palynomorphs in studying the hydrocarbon potential of geologic areas (i.e., determining whether petroleum-forming conditions had been encountered in the past by source rocks), but he went no further than this. We have found that a particular manipulation in collecting and in using data concerning carbonization of palynomorphs in samples obtained near the surface of the earth can be used for a much more significant purpose: obtaining near-surface data that directly indicate the presence or absence and location of a more deep-seated mineral deposit, including petroleum, coal, etc.

2. Description of the Prior Art

The Gutjahr paper has already been mentioned. One of us (Grayson) in a paper "Relationship of Palynomorph Translucency to Carbon and Hydrocarbons in Clastic Sediments" at the Centre National de la Recherche Scientifique at Paris 15-17 September, 1973, at the International Colloquium of Petrography, presented data using measurement of the amount of light absorbed by or transmitted through various specific palynomorphs as a key to the measure of carbonization. Specific taxa were selected for the study because translucency characteristics vary among different types of pollen and spores. All measurements were made on the same taxon. It was shown that the percent translucency varied from shallow depths in the well (of the order of 2,500 feet) to depths of the order of 14,000 to 16,000 feet and that the measurements tended to correlate with analyses of samples from the well for carbon, oxygen, nitrogen, and hydrogen. No data on light transmission or absorption from specific taxa collected from samples from shallow locations were given in this paper.

Others in the petroleum industry subjectively utilize palynomorph (visual) color as an indicator of source rock diagenetic maturation. However, study of the literature in the field of palynology indicates to us that others have not made use in hydrocarbon and mineral prospecting of light transmission properties from palynomorphs collected in the shallow subsurface region of wells.

SUMMARY OF THE INVENTION

We have developed a new prospecting method for aid in the location of hydrocarbons or other minerals which is based on measuring the quantity of characteristic of light which is absorbed or transmitted by specific organic particles in geologic specimens taken at at least two different depths. This method is particularly useful in the shallow portion of wells; that is, at depths down to the order of approximately 500 feet or so from the surface. However, the benefits of our new method of prospecting can also be derived at depths in excess of 500 feet.

As will be subsequently shown in greater detail, the rock samples from a single location at two diffreeent depths in the well are processed to recover the organic matter present in the rock. This material is microscopically investigated to locate palynomorphs, preferably of the same taxon. Light absorption or transmission through the specimen is photometrically measured until sufficient data have been obtained to determine the mean percent transmission or absorption. The difference between the mean translucency/absorption data populations for two samples at different depths at the location could be called a differential indicator of diagenesis. The same procedure is carried out for the other samples collected from comparable sections of the other wells, and the differential values, or gradients (that is, the difference divided by the vertical separation between sampling points) are plotted on a map of the region so that it is possible to contour these plotted data. The contoured data tend to form contour lines which encircle a mineral deposit, for example an oil or gas field, even though the deposit usually lies at a greater depth than the greatest depth from which any samples have been taken.

More details on this system are presented in this specification.

BRIEF DESCRIPTION OF THE DRAWINGS

The drawings listed below disclose illustrative embodiments of the present invention when taken in connection with the following detailed description. In these drawing, the use of the same reference numeral in more than one figure indicates the same or a corresponding part.

In these drawings.

SAMPLE LABORATORY TREATMENT

In the work which is being described here, rock samples were treated with 10 percent hydrochloric acid, washed, treated with 70% hydrofluoric acid, washed, and the organic matter differentially separated from remaining minerals with zinc bromide at a specific gravity of 2.2, and microscope slides of the residues were made. No oxidation, staining, or ultrasonic generator treatment were performed on these samples. All samples were maintained in their respective solutions for the same length of time in order to minimize the possible effects of differential treatment. It was early determined that the length of time of the two acid treatments in normal palynological processing does not measurably affect the translucency characteristics of the exine. After the slides had been prepared, they were uniformly studied using a standard binocular research microscope specially supplied with an ocular fitted with a fiber optic probe and electronic amplification equipment, as described below.

Those skilled in this art are well acquainted with the standard precautions observed in collecting the geological samples from which the palynomorphs are obtained, to avoid contamination, mixing, mislocation, and the like.

OBSERVATION AND MEASURING APPARATUS AND ITS USE

Figure 1:
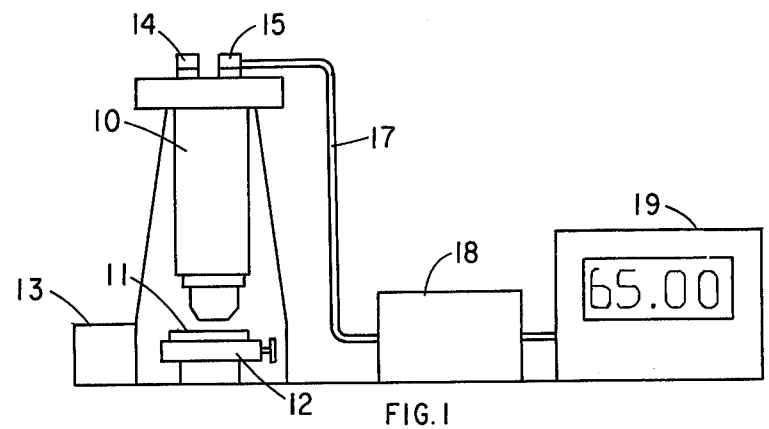
FIG. 1 shows in diagrammatic form elements of apparatus useful in measuring the light transmission properties of palynormorphs.
Figure 2:
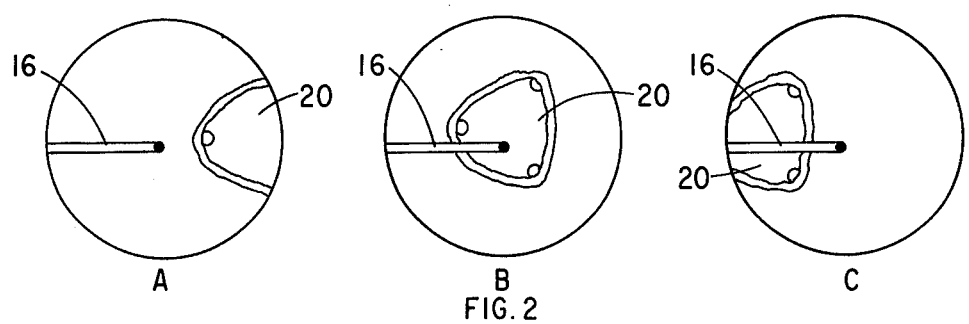
FIG. 2 A, B, and C show a diagram of the appearance in a microscope of a single taxon and indicate how the slide is manipulated to measure the percent transmittance of light utilized in this invention.

Some of the basic elements used in an early form of microscopic study arrangement are shown in FIG. 1. In this figure, the microscope is indicated by numeral 10, and the slide by 11. The mechanical microscope stage is indicated as 12 and the illuminating light source by 13. The oculars for the microscope are denoted by 14, and 15, respectively. It is to be noted that one ocular 15 has been internally and permanently fitted with a fiber optic probe. (A suitable probe is Model No. 700-3B, obtainable from Gamma Scientific, Inc. This was mounted in a 10x ocular for a standard binocular research microscope.) The tip of the probe 16 is shown in FIG. 2 as it appears to an observer employing this ocular. The apparent black dot at the right extremity of the probe is the fiber optic tip which has been optically polished and which is terminally recurved 90° to extend away from the observer, so that the light intensity in the ocular can be suitably sampled. As an illustration, the diameter of such a probe is $4.5 \times 10^{-4}$ meters, corresponding to a cross-sectional area being sampled of $1.59 \times 10^{-7}$ square meters.

This fiber optic probe is connected by a flexible optic tube 17 to a photomultiplier 18, which, when its shutter is open, produces an amplified output signal directly proportional to the illumination of the probe tip. This multiplier 18 in turn is connected to a photometer 19, which is essentially a vacuum tube voltmeter of a very stable sort. A suitable set of equipment is the photomultiplier Model EMI9502, from Gamma Scientific, Inc.., and a photometer, Model 2020A (same source.) Additional equipment employed was standard and, therefore, is not illustrated. It might be mentioned that the light source 13 was maintained at constant voltage by a voltage regulator so that minimum attention need be paid to reproducibility of ratings on the digital readout of the photometer.

In using this apparatus, it is assumed all apparatuses have been turned on and steady-state operating conditions prevail. The object to be measured (that is, one of the palynomorphs on the slide 11) is located in the field of view of the microscope by suitable manipulation of the microscope stage, and a procedure shown in FIG. 2 is employed to measure the light translucency, or absorption. The object is manipulated by suitable adjustment of the mechanical stage 12 until the tip of the fiber optic probe 16 is located in a clear area on the slide adjacent to the particular palynomorph 20 to be measured (see A, FIG. 2). The shutter of the photomultiplier 18 is opened and the photometer 19 adjusted so that the output meter reads 100; this may be on any desired scale and is simply to get a base reading against which the translucency will be determined. The microscope slide is then moved so that the tip of the fiber optic probe is over the selected area of the palynomorph to be measured (see B, FIG. 2) and a reading is taken. A reading of 65, for example, would mean that 65 percent of the light illuminating the slide has been transmitted through the specimen, and 35 percent of this light has been absorbed. The slide is again moved so that the tip of fiber optic probe is again sampling illumination in a clear area adjacent to the same particular specimen, but preferably on the specimen's other side (see C, FIG. 2) and the third reading is checked against the first. Ordinarily, a reading of 100 is again found on the photometer. If the check reading varies perceptibly from 100, the measurement is discarded and the procedure repeated. We have found in actual practice that it is infrequent for check reading to be more or less than $100 \pm 1$ percent. When this does occur, it is usually due to a particle being present in the path of the light that was not observed because it was out of focus when the object measured is in focus. Occasionally, a deviation occurs if the operator inadvertently changes the focus on the specimen during the measurement. It is important that the object to be measured be in focus before the initial check measurement is made, and that no change of focus be made before the final check measurement. A change in focal level alters the amount of light transmitted and, therefore, changes the standard. Since the equipment is extremely sensitive to light, it is desirable to operate the equipment in subdued lighting and to cap the ocular containing the fiber optic probe with a light-tight cap before making measurement.

Since the amount of light transmitted through various microscope objectives differs substantially, it is desirable to use the same objective throughout.

We generally prefer to make measurements on enough specimens such that the computed mean is, with a 95 percent confidence level, with $\pm 2.5$ percent of the true mean value. Experience indicates that averaging 30 measurements exceeds these criteria.

After the translucency has been measured for a single specimen on the slide, one proceeds to select and measure another specimen on the same slide, and so on, until sufficient readings have been obtained so that a statistically significant average has been ascertained. This of course depends upon the variation in the readings, which in turn depends upon the particular taxon being observed. The microscope technique should be essentially the same for each slide.

Different types of palynomorphs may have different translucency characteristics because of difference in exine (wall) thickness and ornamentation. It is desirable in any particular region to select a type as a standard which will have certain characteristics. Basically the choice is determined by the kind of palynomorph which will give high translucency values at the early stages of organic metamorphism so that the translucency scale will be as wide as possible. A psilate (smooth surfaced), or nearly psilate grain is preferable because ornamentation difuses the light and causes greater variation in the translucency spectrum. A relatively large type is preferred because it is easier to locate and recognize under the microscope, and it offers more exine area for measurement. A medium-thick exine is best because thin exines fold easily, thus eliminating specimens that can be measured, and thick exines absorb too much light so that the translucency range is attenuated. Uniformity is desirable; the fewer aperatures, perforations, scars, etc., that are present, the better the potential type. The more abundant and long ranging a specimen is in geologic time, the better the type. If a type becomes rare or disappears entirely from the section, another type can be selected, and we find that the translucency values of the different types can be adequately related in samples in which they both occur. While the above discussion has dealt with measurements of light transmission or absorption with respect to the visible spectrum, or some part of it, in principle there seems no need to limit such measurements to visible light. Both infrared and ultraviolet radiation produce results rather like that of visible light, and the choice is largely at the convenience of the operator.

DATA COMPILATION

The next step in this process consists of obtaining the difference between the light characteristic, such as the mean percent translucency of the palynomorph populations, obtained at two different vertical depths in the same or very closely spaced shallow wells. Preferably, the vertical difference between the two sample locations at one station should be small compared to the distance between survey stations, which may well be of the order of a mile or so. The vertical difference between the sample locations should be at least approximately 250 feet and preferably should be of the order of 350 to 400 feet. We prefer to pick a minimum sample depth of about 200 to not more than 250 feet. This avoids likelihood of surface contamination of any kind on the shallow samples, and the possibility of surface oxidation (weathering) differentially affecting a population's translucency mean. Again, the approximate maximum depth of the deepest specimen from which palynological measurements are made need not be in excess of approximately 500 feet from the surface, though greater depths may be used.

The datum to be contoured is called the Differential Diagenetic Index (DDI). It consists of the difference between the means of the measured light characteristic (such as percent translucency or percent absorption) at the two depths chosen in a particular geographic location, such as a single well. Clearly, this datum from each set of measurements at two vertically separated sampling points is proportional to the gradient of the light characteristic, and in fact is this gradient multiplied by this vertical separation. As long as the data to be contoured have been obtained from sets of samples in which the vertical distance between sampling points is conparable, there is no need to obtain the ture gradient, as stated above. However, if such vertical distances vary more than about ± 20 percent, we prefer to plot and contour the true gradient, which simply requires that each such differential be divided by the corresponding vertical distance between the sampling points. These quotients, or numbers directly proportional to such gradients, are then plotted. We want it clearly understood where reference is made to the term "Differential Diagenetic Index" or "DDI" in the balance of this specification or the appended claims, such term includes both the difference in the light characteristic, and the true gradient as discussed above. Ordinarily, the measured mean translucency for the lower sampled palynomorph will be less than that for the upper, due to increased diagenesis of the taxon as a function of depth/temperature; hence, increased carbonization and consequent greater opacity..

DATA INTERPRETATION

The last step consists in plotting the DDI on a map of the region from which the samples came, and in contouring these data.

Figure 3A:
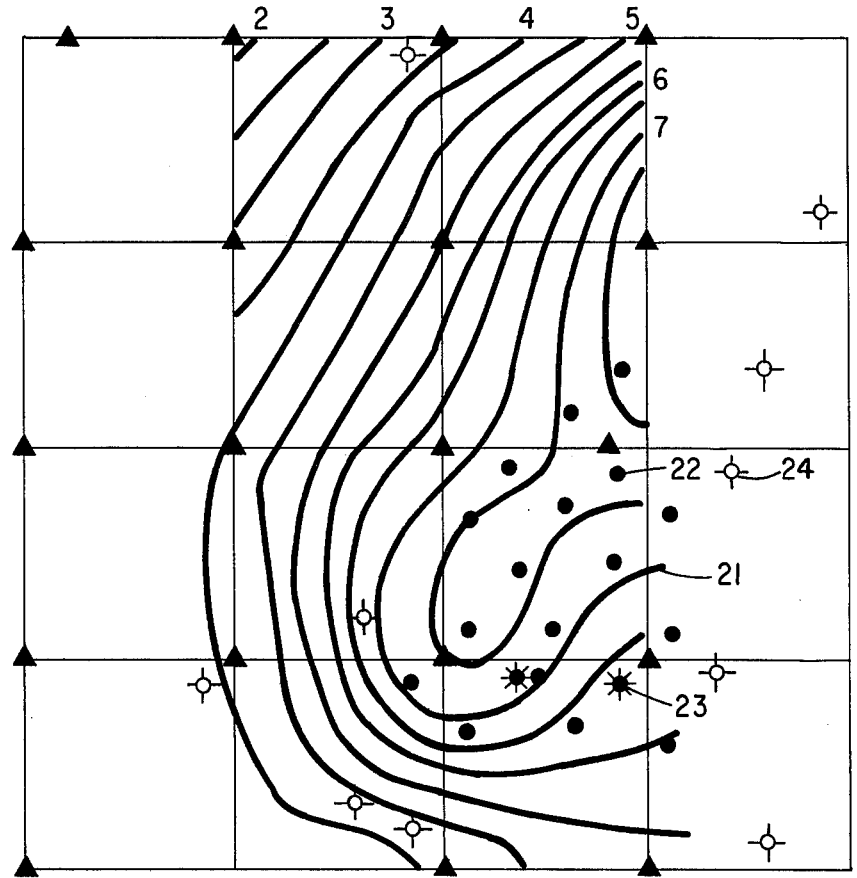
FIG. 3 shows in two parts, (A) and (B), a map of a region including an oil field and differential percent translucency contour lines prepared by use of this invention which outline this particular field.
Figure 3B:
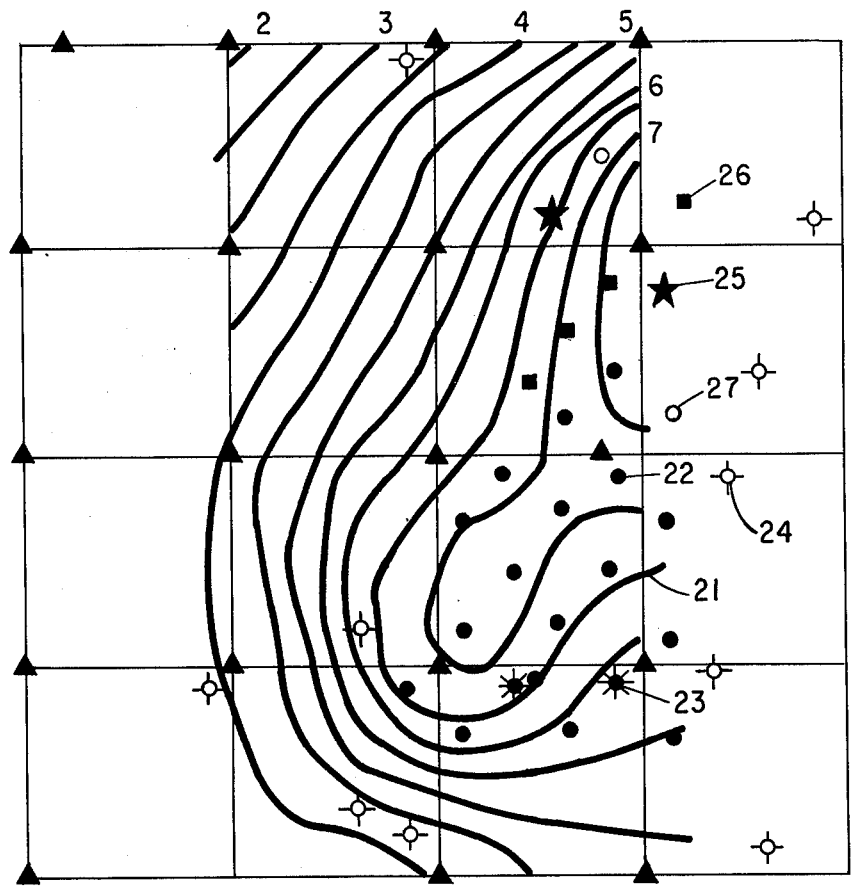

A suitable example of such use of actual data is shown in FIGS. 3A, 3B.

in FIGS. 3A and 3B, the basic grip (the horizontal and vertical lines) are the section lines for a particular region in and around an oilfield, where drilling was in progress at the time the samples were gathered.

The samples were obtained at some of the spots located on this map by the large black triangles which are essentially a mile apart. In this particular case, the geologic samples at the varying depths came from a series of shallow core holes, drilled approximately 500 feet deep. The procedure outlined above was followed, employing the fiber optic probe in a microscope ocular and following the criteria that the palynomorphs from which the DDI was obtained in each case were separated by a vertical distance of the order of 250 feet corresponding to a 200-foot and a 450-foot specimen depth. The particular taxon used in this case was Proteacidites. The resulting DDIs were then automatically contoured with the use of a standard computer program. The resultant contour lines 21 are shown in FIGS. 3A and 3B and correspond to a range from high to low of approximately 7.5 to 2.

It is seen that the contours increase in the direction of the field and, in fact, outline a nose-like or crudely oval anomaly centered in the third section from the lower left corner and the second section up. Also plotted in FIGS. 3A and 3B are the locations of the producing oil wells, indicated by the circular black dot 22, the location of producing gas wells indicated by the circular black dot with crosses 23, and the dry holes indicated by open circle with a single cross 24, which outline the boundaries of this particular field. The wells in FIG. 3A were drilled before obtaining the DDI palynological data. It is to be noted that the contour lines in FIG. 3A indicating the anomaly on the DDI do quite adequately outline what had been the southern limits of this field; in fact the specific contour line 21 is very nearly a defining contour between the region of producing wells and dry holes. In this particular case, the field produces from a depth of approximately 7,400 feet, so it is readily apparent that the prospecting depth (which it must be remembered was a maximum of about 500 feet from the surface) was not adjacent to the producing horizon, but did adequately define it.

Contour line 21 also indicates the possible existence of a field extension to the northeast.

FIG. 3B illustrates the historical development of field extension wells drilled after the collection of palynological data. The DDI contours quite clearly predicted the success of the field extension wells, both in terms of "hit or miss", and initial production rates from the wells.

The four new wells indicated by solid squares 26 are producing wells drilled since the analysis of translucency data. The two starred wells were very recently drilled. Both are "shut-in" pending pipeline installation. Starred well 25 has already tested unusually high in terms of oil and gas production rates as would be predicted from FIG. 3. More wells (open circles 27) are scheduled to be drilled within the contoured trend.

It should be apparent to those skilled in this kind of work that the method taught above is flexible in use and permits considerable modification. For example, the laboratory treatment may be varied as to concentration of the mineral acids used, contact time, washing, etc., in advance of selecting the specimens. The observation and measuring apparatus has been changed, though the type of data desired is the same. In fact, other radiation than visible light may be employed. Insofar as use of the data is concerned, we prefer to contour the differential of the light translucency and, if large changes in vertical separation of specimens is involved, to divide this difference by the separation to obtain a true gradient before contouring. However, some indication of the presence of a mineral deposit can be obtained from alternate techniques, still within the scope of the appended claims. This includes the preparation of sections (cross sections) of the subsurface from well to well across an approximate line from one side of a region to the other. It also includes mapping or contouring the data from one level of specimens, that is, without subtracting one reading at one level from the other at a different level. Basically, this last system is simple, but the results will usually be found to be less diagnostic than the use of the DDI.

We do not wish to be bound by any specific theory in this prospecting method. However, we do believe that many of the mineral deposits of the earth individually have more or less thermal energy than is present in rocks adjacent to the deposits. This may be true at present or may have been true in past geologic time. Because of this temperature anomaly in the earth's crust, the thermal gradient between the point of anomalous thermal energy and the surface of the earth is in turn either more or less than the thermal gradient in the adjacent rocks at equivalent depth. It appears that this difference in the thermal gradient, then is reflected in the level of diagenesis in the organic matter present in the rock above the hydrocarbon or other mineral deposit. Specifically, it is found that considerable thermal anomalies were involved in formation of deposits of minerals such as petroleum, coal, lead, zinc, and the like. This, then, is the cause for diagenetic changes in the taxa, and lies at the base of this diagnostic system for locating such mineral deposits. The level of organic diagenesis can be measured by a characteristic of light as detected by photometric equipment, as discussed above. The difference in levels of DDI, for example, which can be contoured using this technique, may be due to a present thermal gradient or to a paleothermal gradient. In either case, as we have shown, anomalies in the DDI data are useful in prospecting for the presence or proximity of the mineral deposits located deeper in the earth.

It is apparent rom this discussion that the lateral distance between sampling stations may vary considerably depending on the desired detail in the contouring. In a regional survey, a separation of several miles may be used, while a mile or less may be desirable for more detailed outlining of areas of interest. The total change in values is also a factor, as is the lateral rate of change in values.

We claim:

1. A method of prospecting comprising the following steps:
   (a) removing palynomorphs from geological samples collected from a plurality of stations separated by a considerable distance in a region and,
   (b) measuring a light characteristic due to transmission of light through a selected part of each of a plurality of said palynomorphs recovered from each sample to determine an average value thereof, whereby the average values from step (b) may be mapped against the location of said plurality of stations to produce anomalies characteristic of the subsurface below said stations.

2. A method in accordance with claim 1 in which in step (a), said geological samples were collected from pairs of locations at each of said stations, said pairs of locations being vertically separated over a hundred feet, whereby a differential diagenetic index (DDI) can be computed for each said station by taking the difference in said average values of said light characteristic corresponding to each of said pairs of locations, and the values of said DDI can be plotted against the location of said stations and such values contoured, by means of which anomalies characteristic of mineral deposits may be recognized.

3. A method in accordance with claim 2 in which said pair of locations are at least approximately in vertical alignment, said palynomorphs are of the same or at least of a closely related taxon, and said light characteristic is the translucency of at least a part of the exine of said palynomorphs.

4. A method in accordance with claim 3 in which said pair of locations are vertically separated in a well in the earth's crust, the upper locations at a sample depth of about 200 feet, with said vertical separation being at least approximately 200 feet, all of said palynomorphs are of the same morphologic type, and said measurement of light transmission is through a portion of the exine of each of said palynomorphs of comparative uniformity.

5. A method in accordance with claim 4 in which the percent translucency to visible light of said portion of said exine is measured on sufficient number of specimens from each said locations so that the computed mean is, with a 95 percent confidence level, within ± 2.5 percent of the true mean value.

6. A method of prospecting comprising the following steps:
   (a) drilling a plurality of wells to a depth of about 500 feet in a selected region.
   (b) collecting geological samples from the formations forming the walls of said well at a pair of locations vertically separated by at least 250 feet,
   (c) processing each of said samples chemically by substantially the same method, including dissolving carbonates by hydrochloric acid and silicates by hydrofluoric acid, to obtain an organic residue which has not been substantially oxidized by the process and mounting the resulting organic residue on microscope slides,
   (d) investigating said slides microscopically at the same magnification to identify on each slide a plurality of specimens of a prechosen morphologic type of palynomorph, and for each of such specimens measuring microphotometrically the percent translucency through at least a portion of the exine of such palynomorph in an essentially uniform location, (e) averaging separately the percent translucency of said palynomorphs from each such sample, (f) forming a Differential Diagenesis Index (DDI) for each such well by obtaining the difference in the average percent translucency for said palynomorphs at each said pair of locations, and (g) plotting on a map of said region at the location of said wells the corresponding values for said DDI contouring said values on said map, whereby anomalies in said contours may be used to aid in prospecting said region.

* * * * *